United States Patent [19]

Gordon et al.

[11] Patent Number: 4,705,630

[45] Date of Patent: Nov. 10, 1987

[54] CENTRIFUGATION

[75] Inventors: Alan J. Gordon, Liverpool; Donald G. Billington, Stoke on Trent; Robert Evans, Liverpool; David J. Bowman, Manchester, all of England

[73] Assignee: Shandon Southern Products Limited, Runcorn, England

[21] Appl. No.: 871,530

[22] Filed: Jun. 6, 1986

[30] Foreign Application Priority Data

Jun. 10, 1985 [GB] United Kingdom ............. 8514591

[51] Int. Cl.⁴ ............................................. B01D 33/22
[52] U.S. Cl. ................................... 210/361; 210/927; 422/72; 422/102
[58] Field of Search ............. 210/361, 781, 927, 782, 210/541, 542, DIG. 24; 422/101, 72, 73, 102

[56] References Cited

U.S. PATENT DOCUMENTS 4,391,710  7/1983  Gordon ........................ 210/361

Primary Examiner—Frank Sever
Attorney, Agent, or Firm—Vaden, Eickenroht, Thompson & Boulware

[57] ABSTRACT

Centrifugation apparatus characterized by a carrier including both a bucket to accommodate a sample chamber and means for supporting a specimen container adjacent to the sample chamber so that material in the specimen container can be pre-centrifuged and then transferred to the sample chamber for centrifugation therein, using automated transfer means. The apparatus may include a disaggregator cooperable with the specimen container to disperse the contents of the latter prior to pre-centrifugation. The transfer means may be a pipette with arrangements for both external and internal flushing and measured dilution of a transferred sample. There may also be means for supplying treatment fluid to a reservoir of the sample chamber.

9 Claims, 7 Drawing Figures

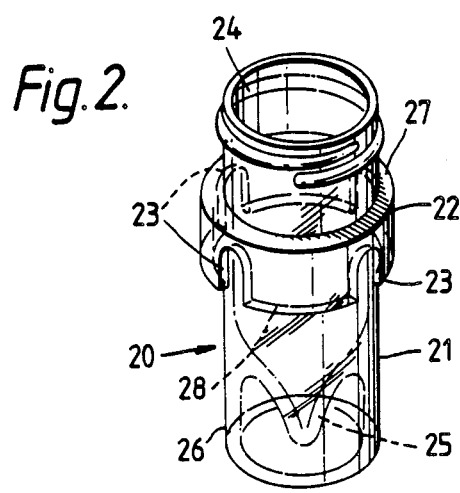
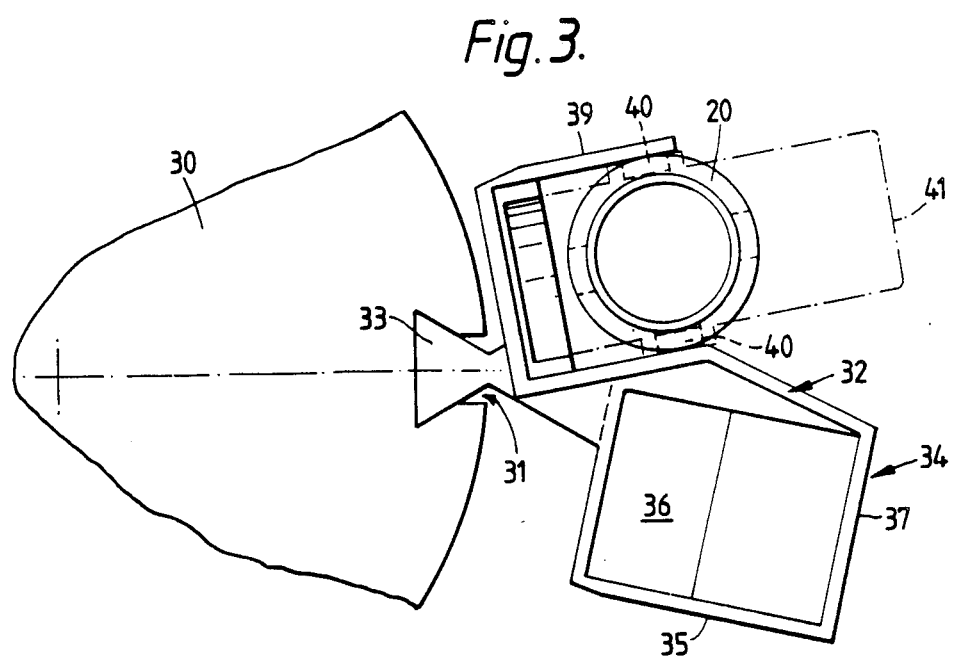

४,705,630

CENTRIFUGATION

FIELD OF THE INVENTION

This invention concerns centrifugation of suspensions to effect separation of solids therefrom for, e.g., microscopic examination. The invention is especially concerned with the centrifugation of body fluid and like samples comprising cell suspensions to accomplish the deposition of a cell layer on a slide or other receiving surface for cytological examination, a general objective of the invention being to facilitate and improve the preparation of such cell layers in routine cytological screening procedures, e.g., in the screening of cervical cell samples for carcinoma.

A more specific objective of the invention is to provide for significant automation in the handling and processing of collected cell samples to produce cell deposits on a slide or the like and, especially, to produce monolayers of deposited cells for automated examination by optical scanning devices.

BACKGROUND TO THE INVENTION AND THE PRIOR ART

It is known to place a cell suspension in a generally tubular sample chamber having an open end juxtaposed to the surface of a microscope or like slide, with the interposition of an apertured filter card that both provides a seal between the sample chamber and the slide surface and also serves to absorb the liquid components of the suspension. The assembly of sample chamber, slide and filter card is subjected to centrifugation to cause the deposition of a layer of cells on the slide surface and the removal of the suspension liquid into the filter card. One example of cytocentrifugation apparatus especially adapted to perform this cell separation and deposition technique is disclosed in U.S. Pat. No. 4,391,710.

The cell suspension that is submitted to centrifugation generally requires some preparatory treatment, especially when it is desired that the centrifugation shall produce a monolayer of deposited cells uniformly dispersed over a relatively large receiving surface area so as to be suitable for automated examination by optical scanning devices. Thus typically cell samples obtained by scraping ("smear") techniques are collected in specimen containers that are filled with a collection fluid to preserve the cells while in transmit from a collection centre to a laboratory. When the collection containers are received by the laboratory the cells of the specimens therein have usually aggregated and need, therefore, to be disaggregated, for instance by stirring in the collection fluid. This leads to a relatively small quantity of cells becoming dispersed in a relatively large volume of collection fluid and it is necessary to allow the cells to settle to enable a suitably concentrated sample to be obtained for the centrifugation procedure. This settlement may, for instance, be accomplished by precentrifugation to form a packed cell button, a sample of which may be then taken as by pipette, diluted with a suitable volume of suspending liquid and then placed in the sample chamber of the centrifuge.

These preparatory sample treatment procedures are time-consuming and labour intensive and by their nature can easily lead to dissociation of a particular cell specimen from the records relating to the donor patient.

A further and more specific object of the invention is therefore to facilitate the carrying out of these preliminary procedures, as necessary for any particular type of cell specimen, and to minimise the risk of misidentification of the donor or source of a particular cell deposit as produced by the centrifugation.

SUMMARY OF THE INVENTION

The present invention provides centrifugation apparatus that is characterised by a carrier including both a bucket adapted to accommodate a sample chamber and means for supporting a specimen container in proximity to such sample chamber to enable centrifugation of material in the specimen container and subsequent transfer of centrifuged material from the specimen container to the sample chamber for centrifugation therein.

The sample chamber and the specimen container may each take a variety of different forms subject to the requirement that at least when the carrier is at rest the sample chamber and the specimen container are both supported thereby in an orientation that permits the transfer of centrifuged material from the specimen container to the sample chamber. Preferably, however, the sample chamber is of the construction described in co-pending patent application Ser. No. 871,081 filed concurrently herewith assigned to the assignee of the present application.

The carrier is preferably adapted to support the specimen container pendulously so that this may align itself with the instantaneous gravitational field (natural or artificial) acting thereon.

In its preferred embodiments, the apparatus of the invention includes transfer means registrable selectively with a specimen container and with a sample chamber carried by said carrier, and operable to transfer material from the specimen container to the sample chamber.

Thus conveniently the carrier is adapted at rest to support a specimen container and a sample chamber at a common radial distance from a centrifugation axis and said transfer means comprise a pipette also at said common radial distance from the centrifugation axis whereby registration of the pipette with the specimen container or with the sample chamber, respectively, may be accomplished by indexing said carrier about the centrifugation axis, or by translating the transfer means relative to the centrifugation axis. Alternatively the carrier may be adapted at rest to support a specimen container and a sample chamber on a common radius to the centrifugation axis and the transfer means be arranged to move along said radius with the carrier stationary in a suitable indexed position.

The apparatus may also, optionally, include disaggregator means cooperable with a specimen container supported by the carrier, to disaggregate material in said container. The disaggregator means may, for instance, comprise a probe located at the radial distance of the specimen container from the centrifugation axis and be associated with means for introducing the probe into a specimen container supported by the carrier at rest, and with means for vibrating the probe therein. The means for vibrating the probe in a specimen container may be adapted to cause vibration at an ultrasonic frequency.

When the sample chamber is of the construction disclosed in said co-pending patent application Ser. No. 871,081 and includes a reservoir for a treatment fluid, such as a fixative, the apparatus may conveniently include dispenser means co-operable with such a sample chamber carried by the carrier, for providing a treatment fluid to the treatment fluid reservoir of such sample chamber.

Conveniently the dispenser means comprises a dispensing pipette disposed at the radial distance of the sample chamber treatment fluid reservoir from the centrifugation axis to enable its registration with the sample chamber reservoir to be accomplished by appropriate indexing of the carrier about the centrifugation axis.

In preferred embodiments of the invention the carrier is detachably associable with a centrifuge head so that the carrier may be loaded with a specimen container and with a sample chamber while detached from the centrifuge head—possibly under conditions of containment—and thereafter be attached to the centrifuge head.

Centrifugation apparatus in accordance with this invention permits sigificant automation of the production of examinable deposited cell layers from body fluds and other cellular material received in a specimen container, while also providing for reliable association of the cellular material with the donor patient throughout the collection, preparative and examination procedures.

BRIEF DESCRIPTION OF DRAWINGS

FIG. 2 is a perspective view of a preferred specimen container;

FIG. 3 is a fragmentary plan view of a detachable carrier fitted to the centrifuge head of the apparatus of FIG. 1 and supporting a specimen container of the form shown in FIG. 2;

DESCRIPTION OF PREFERRED EMBODIMENTS OF THE INVENTION

Figure 1A:
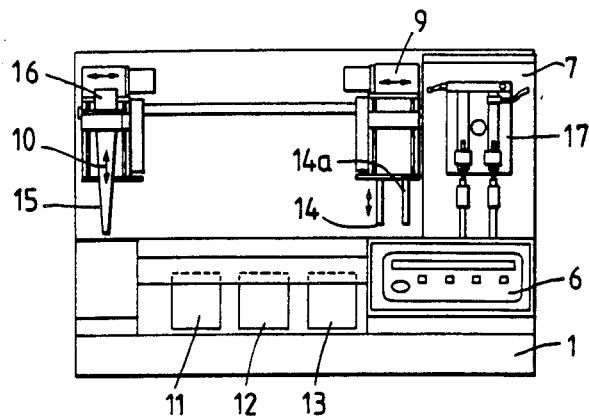
FIG. 1, comprising FIGS. 1a, 1b, 1c, that are respectively front elevation, side elevation and plan views, schematically represents the layout of a centrifugation apparatus embodying the invention.
Figure 1B:
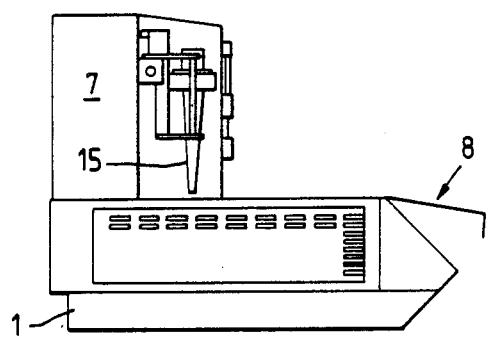
Figure 1C:
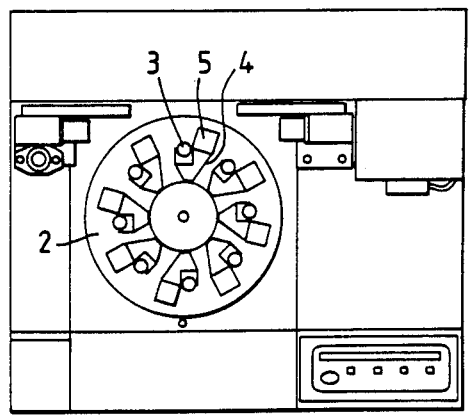

Referring to the drawings, FIG. 1 illustrates schematically the layout of one form of centrifugation apparatus embodying the invention. This apparatus comprises a base 1 housing a drive motor and various control equipment (not shown) for accomplishing both indexing and continuous rotation of a centrifuge head 2 that for simplicity of illustration has been shown as a simple disc structure but that is preferably similar in construction to that of the cytocentrifuge disclosed in U.S. Pat. No. 4,391,710, comprising a containment bowl with removable cover constituting a sealable head assembly within which a carrier plate is disposed.

The centrifuge head 2 is adapted to carry a plurality of sets each including a specimen container 3 and a sample chamber with associated deposit-receiving slide. Each such set is carried by an individual carrier 4 which includes a bucket 5 that accommodates the sample chamber, while providing support for the specimen container 3 of the set so that the sample chamber and the specimen container have a fixed relationship to one another in relation to the vertical centrifugation axis of the head 2. In the arrangement of FIG. 1, this relationship is such that the specimen container 3 is at the same radial distance from the centrifugation axis as the entry to a sample reservoir of a sample chamber in the bucket 5 of carrier. In other embodiments the carriers may provide for the sample chamber and specimen container of a set to be on a common radius to the centrifugation axis.

A control panel 6 is provided at the front of the base 1 of the apparatus and at the rear of the latter there is an upstanding housing 7 that supports a hinged transparent cover (not shown) and provides a mounting for transfer means shown generally at 9 and for disaggregator means shown generally at 10. The base 1 provides an enclosure for fluid containers 11, 12 and 13 accessible through a hinged cover 8.

The transfer means 9 comprises a transfer pipette 14 movable vertically on a carriage that is itself translatable on rails on the front of housing 7, by appropriate mechanism disposed within the housing 7, so that the transfer pipette 14 is capable of being introduced into a specimen container 3 and operated to withdraw a sample of material from the latter that is then transferred to the sample reservoir of the associated sample chamber by raising of the pipette 14, movement of the latter into position over the associated sample chamber and lowering of the pipette for discharge of the sample into the sample reservoir. The transfer means also includes a dispenser pipette 14a on the same carriage as the pipette 14 and adapted, when the pipette 14 is positioned to register with a specimen container 3, to register with a treatment fluid reservoir of the associated sample chamber.

The disaggregator means 10 comprises a probe 15 with associated vibrator 16 all arranged for vertical movement on a carriage translatable horizontally on the housing 7 so as to enable the probe 15 to be introduced into a specimen container 3 and to be vibrated therein, preferably at an ultrasonic frequency, so as to accomplish disaggregation of cellular material in the specimen container.

The fluid containers 11 and 12 may for instance contain a suspension fluid such as saline solution and a cell layer treatment fluid such as fixative, respectively, the container 11 being associated with the pipette 14 and with a washing system for the disaggregator probe 15, while the container 12 is associated with the dispenser pipette 14a of the transfer means 9 for dispensing of the contents of the container 12 into a treatment fluid reservoir of a sample chamber. A pump system shown schematically at 17 serves to feed fluids from the containers 11, 12, to the respective pipettes and to the washing system of the probe 15.

The apparatus as thus far described with reference to the schematic illustration of FIG. 1 is intended to accomplish, in fully automated manner, the pretreatment of a cellular material contained in each of the specimen containers 3, followed by the deposition of a monolayer of cells on a slide by a sequence of steps as follows:

1. Travel of the disaggregator means 10 from its illustrated "parking position" to the right as seen in FIG. 1a to enable introduction of the probe 15 of the disaggregator means 10 into the specimen container 3 referenced in FIG. 1c, followed by vibration of the probe 15 to cause disaggregation of the cells of the material in such container and their dispersion into the collection fluid therein, the probe being withdrawn at the completion of this step, returned to its "parking position" and washed with fluid from the container 11.

2. Indexing of the centrifuge head 2 to bring the next specimen container into registration with the disaggregator means and repetition of step 1;

3. Repetition of step 2 as appropriate to accomplish disaggregation of the material in all specimen containers, followed by return of the disaggregator means 10 to its "parking position";
4. Continuous rotation of the centrifuge head 2 about its centrifugation axis at a sufficient speed to cause the cells suspended in the collection fluid in each specimen container 3 to settle into a cell button therein;
5. Translation of the carriage of the transfer means 9, from the "parking position" shown, to the left as seen in FIG. 1a to position the pipette 14 in register with the specimen container 3 referenced in FIG. 1c.
6. Operation of the pipette 14 to withdraw from the specimen container a predetermined volume of the cell button therein, followed by washing of the exterior of the pipette with a preselected volume of suspension fluid drawn from the container 11, the washing being discharged to the container 3;
7. Travel of the transfer means 9 to the right as seen in FIG. 1a to position the pipette 14 for discharge of its contents to the associated sample chamber in the bucket 5, followed by discharge of a preselected volume of suspension fluid from the container 11 into the sample chamber and to effect internal flushing of the pipette 14.
8. Indexing of the centrifuge head 2 to position the next set of specimen container and sample chamber in registration with the transfer means 9, and repetition of steps 6 and 7;
9. Repetition of step 8 an appropriate number of times to provide each sample chamber with a cell sample from its associated specimen container;
10. Continuous rotation of the centrifuge 2 at an appropriate speed to cause deposition of a monolayer of cells on the slide associated with each sample chamber.

If the sample chamber construction is appropriate, a treatment fluid such as a fixative may be drawn from the container 12 and supplied through pipette 14a to the treatment fluid reservoir of each sample chamber in a manner to accomplish the required treatment of the deposited cell monolayer on the associated slide. This procedure may be accomplished, for each sample chamber, concurrently with step 6 described above, by an appropriate operation of the pump system 17, or by an appropriate additional sequence, depending upon whether a sample chamber provides for precharging a reservoir thereof with treatment fluid or whether this must be supplied to the sample chamber after step 10 above. If the the sample chamber is for instance constructed in accordance with the disclosure of copending patent application Ser. No. 871,081, the treatment fluid from the container 12 may be introduced into a treatment fluid reservoir of each sample chamber contemporaneously with the withdrawal of a cell material sample from the associated specimen container at step 6. In that event, step 10 would be followed simply by stopping of the centrifuge to allow the treatment fluid to pass to the deposition chamber of each sample chamber, and then running up the centrifuge again to an appropriate speed to distribute the treatment fluid over the deposited cell monolayers.

As noted, in preferred realisations of this invention the centrifuge head 2 is fitted with carriers that, preferably, are detachable and that are arranged to support the specimen container and sample chamber of each set thereof in side-by-side relationship at a common distance from the centrifugation axis. FIGS. 2 to 5 illustrate components of apparatus providing this feature.

Thus FIG. 2 shows a preferred form of specimen container 20 that comprises a tubular body 21 having a collar 22 with two pairs of diametrically opposed notches 23 to co-operate with carrier trunnions an externally screw threaded open end 24 to receive a closure cap (not shown) and an internally taped closed end 25 providing a pocket into which cellular material may settle under centrifugation to form a packed cell button. The closed end of the container 20 is formed with a skirt 26 that provides a base on which the container may stably stand. The container is conveniently an injection moulding of transparent plastics material, such as polycarbonate, and for convenience of moulding and economy of material, the collar 22 is desirably an annulus having an internal diameter larger than the external diameter of the body 21 but moulded integrally therewith and connected thereto by a flange 27 and webs 28 at intervals around the body 21.

FIG. 3 illustrates, schematically, part of a centrifuge head 30 formed with dovetail slots at intervals around its periphery, only one such slot being shown at 31. A carrier 32 with a complementary dovetail tongue 33 is detachably connected thereby to the head 30.

Figure 4:
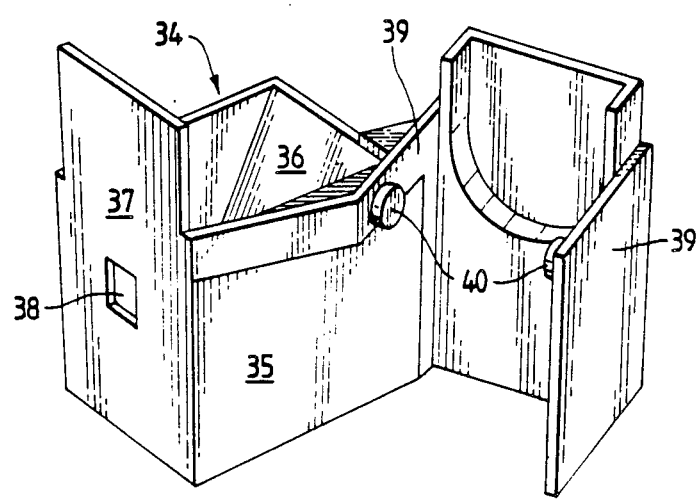
FIG. 4 is a perspective view of the detachable carrier as shown in FIG. 3.

The configuration of the carrier is best seen in FIG. 4, but FIG. 3 shows that it includes a bucket 34 in the form of a frame 35 generally rectangular in plan and arranged relatively to the tongue 33 so that its inboard and outboard walls, 36 and 37 respectively, are perpendicular to a radius to the centrifugation axis of the centrifuge head 30, the outboard wall 37 being parallel with the centrifugation axis whereas the inboard wall 36 slopes downwardly and outwardly to complement the shape of a sample chamber to be received in the bucket 34. The outboard wall 37 has a notch 38 (FIG. 4) to receive a retaining tang on the sample chamber.

The carrier 30 also has a yoke 39 with trunnions 40 for engagement by either of the pairs of notches 23 of the specimen container 20, so that this is pendulously supported by the carrier and is enabled to swing from the rest position illustrated in full lines (in FIG. 3) to the position shown in broken lines 41 under the influence of the radial centrifugal field when the centrifuge 30 head rotates about its axis. The trunnions 40 are at the same radial distance from the centrifugation axis as the sample reservoir of a sample chamber fitted to the bucket 32 so that at rest the specimen container 20 and the sample reservoir are at a common radial distance from the centrifugation axis and may be brought into register with a transfer device, such as the pipette 14 of FIG. 1, merely by indexing the centrifuge head 30, and/or by translation of the transfer device, as above described.

Figure 5:
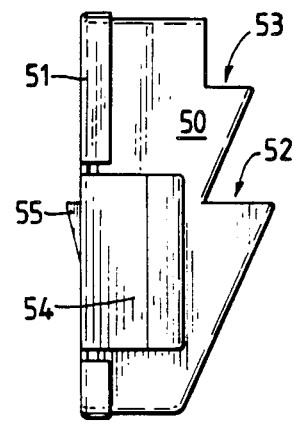
FIG. 5 is a perspective view of a sample chamber such as may be accommodated by the bucket of the carrier of FIGS. 3 and 4.

A suitable sample chamber, of the construction described in detail in said co-pending patent application Ser. No. 871,081, is illustrated in FIG. 5. This sample chamber comprises a body 50 conveniently formed as a moulded of a suitable plastics material, having a rear door 51 attached to the body by an integral plastics hinge. Internally the body 50 has a deposition chamber (not shown) that is generally rectangular in vertical section and that communicates via a slot (not shown) with a sample reservoir 52, the arrangement being such that, as explained in our said co-pending Application, material placed in the reservoir 52 can only reach the deposition chamber when the sample chamber is subject to a horizontal artificial gravitational field. The sample chamber further includes a treatment fluid reservoir 53 that communicates with a buffer chamber (not shown) and thence with the sample reservoir 52 in a manner that provides for transfer of a treatment fluid from the reservoir 53 to the reservoir 52 and thence to the deposition chamber in response to successive changes of the effective gravitational field from vertical to horizontal to vertical and to horizontal.

The rear door 51 serves to secure a filter card and slide in place to receive a deposit of material subject to centrifugation in the deposition chamber, the door 51 being secured by a latch 54. The rear door 51 also has a tang 55 to engage in the notch 38 of the carrier bucket to prevent vertical movement of the sample chamber in the bucket when subject to centrifugation loads.

The general operation of the apparatus has been described in relation to FIG. 1. However, the automation provided by the apparatus, and the close association of a sample chamber with a specimen container throughout the handling of the sample therein also facilitates automated recordkeeping.

Thus, for instance, bar-coded or like machine-recognisable labelling may be utilised to maintain proper correlation of material with the records of a donor patient. For example, donor patient details may initially be recorded both on a record card and on a specimen container, the latter and the card both carrying parts of a bar-coded tag, other portions of which are available for attachment to the related sample chamber and/or the slide on which a cell deposit is made by the apparatus. When patient details are then entered in collected laboratory records they may be associated automatically with the relevant bar code so that at any subsequent time, machine reading of the relevant label can relate that label to the individual patient in the record collection.

We claim:

1. Centrifugation apparatus comprising a carrier for mounting on a centrifugation head for rotation about the axis thereof, and including both a bucket for accomodating a sample chamber and means for supporting a specimen container in proximity to such sample chamber to enable centrifugation of material in the specimen container and subsequent transfer of centrifuged material from the specimen container to the sample chamber for centrifugation therein.

2. The apparatus of claim 1, in which said carrier is adapted pendulously to support a specimen container.

3. The apparatus of claim 1, including transfer means registrable selectively with a specimen container and with a sample chamber carried by said carrier, and operable to transfer material from the specimen container to the sample chamber.

4. The apparatus of claim 3, in which said carrier is adapted at rest to support a specimen container and a sample chamber at a common radial distance from a centrifugation axis and said transfer means comprise a pipette positionable at said common radial distance from the centrifugation axis.

5. The apparatus of claim 3, including disaggregator means co-operable with a specimen container supported by said carrier, to disaggregate material in said container.

6. The apparatus of claim 5, in which said disaggregator means comprise a probe positionable at said common radial distance from the centrifugation axis, means for introducing said probe into a specimen container supported by the carrier at rest, and means for vibrating the probe therein.

7. The apparatus of claim 6, including dispenser means cooperable with a sample chamber carried by said carrier, for providing a treatment fluid to a reservoir of said sample chamber.

8. The apparatus of claim 7, in which said dispenser means comprise a dispensing pipette positionable at said common radial distance from the centrifugation axis.

9. The apparatus of claim 1, in which said carrier is detachably associable with a centrifuge head.

* * * * *